US00PP17956P2

(12) United States Plant Patent
Hofmann

(10) Patent No.: US PP17,956 P2
(45) Date of Patent: Aug. 28, 2007

(54) ***GERANIUM* PLANT NAMED 'PACLILL'**

(50) Latin Name: *Pelargonium peltatum*
Varietal Denomination: Paclill

(75) Inventor: Christa Hofmann, Radeburg (DE)

(73) Assignee: Elsner pac Jungpflanzen, Dresden (DE)

( * ) Notice: Subject to any disclaimer, the term of this patent is extended or adjusted under 35 U.S.C. 154(b) by 0 days.

(21) Appl. No.: 11/358,889

(22) Filed: Feb. 17, 2006

(51) Int. Cl.
*A01H 5/00* (2006.01)

(52) U.S. Cl. ..... Plt./332

(58) Field of Classification Search ..... Plt./332
See application file for complete search history.

*Primary Examiner*—Kent Bell
*Assistant Examiner*—Annette H Para
(74) *Attorney, Agent, or Firm*—C. A. Whealy

(57) ABSTRACT

A new and distinct cultivar of Ivy *Geranium* plant named 'Paclill', characterized by its upright, outwardly spreading and trailing plant habit; vigorous growth habit; freely basal branching habit; large, double and light purple-colored flowers; and good garden performance.

1 Drawing Sheet

Botanical designation: *Pelargonium peltatum.*
Cultivar denomination: 'Paclill'.

BACKGROUND OF THE INVENTION

The present invention relates to a new and distinct cultivar of Ivy *Geranium* plant, botanically known as *Pelargonium peltatum,* and hereinafter referred to by the name 'Paclill'.

The new Ivy *Geranium* is a product of a planned breeding program conducted by the Inventor in Dresden, Germany. The objective of the breeding program was to develop new vigorous Ivy *Geraniums* with attractive flower coloration.

The new Ivy *Geranium* originated from a cross-pollination made by the Inventor in 2000 of two proprietary selections of *Pelargonium peltatum,* not patented. The cultivar Paclill was discovered and selected by the Inventor as a flowering plant within the progeny from the stated cross-pollination in a controlled environment in Dresden, Germany in 2001.

Asexual reproduction of the new cultivar by terminal cuttings in a controlled environment in Dresden, Germany since 2002 shown that the unique features of this new Ivy *Geranium* are stable and reproduced true to type in successive generations of asexual reproduction.

SUMMARY OF THE INVENTION

The following traits have been repeatedly observed and are determined to be the unique characteristics of 'Paclill'. These characteristics in combination distinguish 'Paclill' as a new cultivar and distinguish it from other known Ivy *Geranium* cultivars:

1. Upright, outwardly spreading and trailing plant habit.
2. Vigorous growth habit.
3. Freely basal branching habit.
4. Large, double and light purple-colored flowers.
5. Good garden performance.

Plants of the new Ivy *Geranium* differ primarily from plants of the parent selections in flower coloration.

Plants of the new Ivy *Geranium* can be compared to plants of the cultivar Paclit, disclosed in U.S. Plant Pat. No. 17,399. In side-by-side comparisons conducted in Dresden, Germany, plants of the new Ivy *Geranium* differed from plants of the cultivar Paclit in the following characteristics:

1. Plants of the new Ivy *Geranium* had closed leaf bases whereas plants of the cultivar Paclit had open leaf bases.
2. Plants of the new Ivy *Geranium* had more umbels per plant than plants of the cultivar Paclit.
3. Plants of the new Ivy *Geranium* and the cultivar Paclit differed in flower color as plants of the cultivar Paclit had darker purple-colored flowers.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Flower and foliage colors in the photograph may differ slightly from the color values cited in the detailed botanical description which accurately describe the colors of the new Ivy *Geranium*. The photograph comprises a side perspective view of a typical flowering plant of 'Paclill' grown in a container.

DETAILED BOTANICAL DESCRIPTION

Plants of the cultivar Paclill have not been observed under all possible environmental conditions. The phenotype may vary somewhat with variations in environment, such as temperature and light intensity, without, however, any variance in genotype.

The aforementioned photograph, following observations and averaged measurements describe plants grown during the summer in containers in Dresden, Germany, and under commercial practice in a glass-covered greenhouse with day temperatures ranging from 18° C. to 20° C., night temperatures about 18° C. and light levels ranging from 15 to 75 kilulox. Plants used for the photograph and the description were about five months old and had been pinched two times.

In the following description, color references are made to The Royal Horticultural Society Colour Chart, 1995 Edition, except where general terms of ordinary dictionary significance are used.

Botanical classification: *Pelargonium peltatum* cultivar Paclill.

Parentage:

*Female, or seed, parent.*—Proprietary selection of *Pelargonium peltatum,* not patented.

*Male, or pollen, parent.*—Proprietary selection of *Pelargonium peltatum,* not patented.

Propagation:

*Type cutting.*—Terminal cuttings.

*Time to initiate roots, summer.*—About 18 days at 22° C.

*Time to initiate roots, winter.*—About 22 days at 22° C.

*Time to produce a rooted young plant, summer.*—About 25 days at 22° C.

*Time to produce a rooted young plant, winter.*—About 30 days at 22° C.

*Root description.*—Fine, fibrous; white in color.

*Rooting habit.*—Freely branching; dense.

Plant description:

*General appearance.*—Upright, outwardly spreading, trailing and eventually cascading plant habit; uniformly mounded; densely foliated.

*Growth and branching habit.*—Vigorous growth habit. Freely basal branching habit with about eight lateral branches per plant.

*Plant height, to top of umbels.*—About 22 cm.

*Plants height, to top of foliar plane.*—About 20 cm.

*Plant width.*—About 30 cm.

*Lateral branches.*—Length: About 15 cm. Diameter: About 3 mm. Internode length: About 3 cm. Texture: Sparsely pubescent. Color: 147B.

*Foliage description.*—Arrangement: Opposite; simple. Length: About 4 cm. Width: About 5 cm to 6 cm. Shape: Palmately-lobed. Apex: Acute. Base: Cordate; closed. Margin: Lobed. Venation pattern: Palamate. Texture, upper surface: Smooth, glabrous; leathery. Texture, lower surface: Slightly pubescent along the veins; leathery. Color: Developing and fully expanded foliage, upper surface: 137A; venation, 147C. Developing and fully expanded foliage, lower surface: 137B; venation, 147C. Zonation pattern: Faint. Location of zone from margin: About 2 cm. Width of zone: About 1 cm. Color: 147A. Petiole: Length: About 3 cm. Diameter: About 2 mm. Texture, upper and lower surfaces: Pubescent. Color, upper and lower surfaces: 144A.

Flower description:

*Flower arrangement.*—Light purple-colored flowers; double rotate flowers arranged in roughly hemispherical umbels arising from apical leaf axils. Umbels displayed above the foliage on strong peduncles. Flowers face upright to outwardly; flowers mostly flat. Flowers not persistent. Flowers not fragrant.

*Quantity of flowers.*—About 17 flower umbels per plant each umbel with about six to seven flower buds and open flowers.

*Flowering season.*—Year-round under greenhouse conditions. In Germany, flowering is continuous from May until frost.

*Flower longevity.*—Individual flowers last about six to ten days on the plant; umbels last about three to four weeks on the plant.

*Umbel diameter.*—About 4.5 cm.

*Umbel diameter.*—About 8 cm.

*Flower diameter.*—About 4.5 cm.

*Flower depth* (*height*).—About 2 cm.

*Flower buds.*—Length: About 1 cm. Diameter: About 5 mm. Shape: Elliptic. Color: 144A.

*Petals.*—Quantity per flower: About five. Length: About 2.5 cm. Width: About 1.5 cm to 1.7 cm. Shape: Obovate. Apex: Rounded. Base: Attenuate. Margin: Entire. Texture, upper and lower surfaces: Smooth, glabrous; velvety. Color: When opening and fully opened, upper surface: 76B; color becoming closer to 76D with development; towards the base, close to 155D; venation, 74A. When opening and fully opened, lower surface: 76D; towards the base, close to 155D; venation, 76D.

*Petaloids.*—Quantity per flower: About 15 to 19. Length: About 1 cm to 1.5 cm. Width: About 5 mm to 15 mm. Shape: Obovate; irregular. Apex: Acute to rounded. Base: Attenuate. Margin: Entire. Texture, upper and lower surfaces: Smooth, glabrous; velvety. Color: When opening and fully opened, upper surface: 76B; color becoming closer to 76D with development; towards the base, close to 155D; venation, 74A. When opening and fully opened, lower surface: 76D; towards the base, close to 155D; venation, 76D.

*Sepals.*—Quantity per flower: About five to six in a single whorl. Length: About 1.2 cm. Width: About 3 mm. Shape: Lanceolate. Apex: Acute. Base: Attenuate. Margin: Entire. Texture, upper and lower surfaces: Sparsely pubescent. Color, upper and lower surfaces: 144A.

*Peduncle* (*umbel stem*).—Length: About 10 cm. Diameter: About 3 mm. Strength: Strong; flexible. Texture: Sparsely pubescent. Color: 144A.

*Pedicel* (*individual flower stem*).—Length: About 2 cm to 2.5 cm. Diameter: About 1 mm to 1.5 mm. Strength: Moderately strong. Texture: Sparsely pubescent. Color: 144A.

*Reproductive organs.*—Androecium: Stamen quantity per flower: About three. Anther length: About 2 mm. Anther shape: Elongated. Anther color: Brownish. Pollen amount: Sparse. Pollen color: Golden brown. Gynoecium: Pistil quantity per flower: One. Pistil length: About 3 mm. Stigma shape: Five-parted. Stigma color: Red purple. Style length: About 1 mm. Style color: Pale green to white. Ovary color: Pale green.

*Seed.*—Seed development has not been observed.

Disease/pest resistance: Plants of the new Ivy *Geranium* have not been observed to be resistant to pathogens and pests common to Ivy *Geraniums*.

Garden performance: Plants of the new Ivy *Geranium* have been observed to tolerate rain, wind, and temperatures ranging from about 0° C. to about 35° C. and have demonstrated good garden performance.

It is claimed:

1. A new and distinct cultivar of Ivy *Geranium* plant named 'Paclill', as herein illustrated and described.

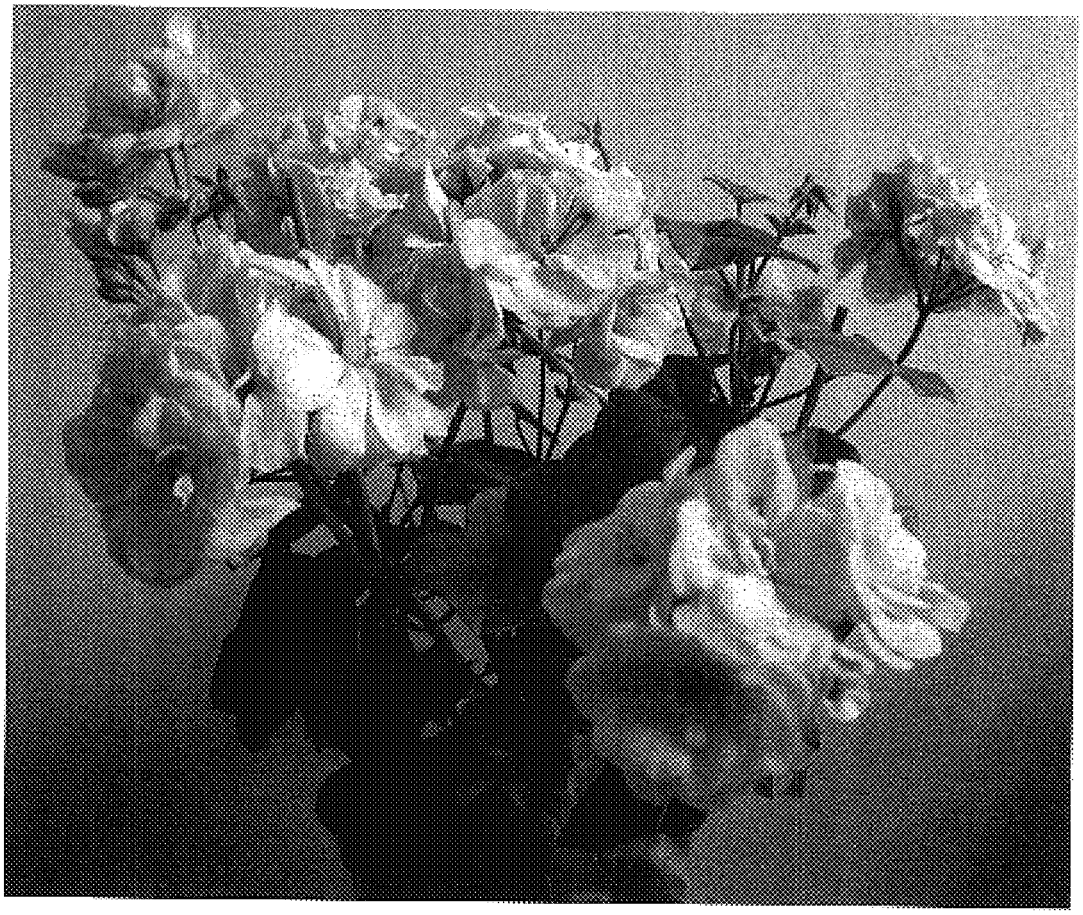

* * * * *